(12) United States Patent
Wu et al.

(10) Patent No.: US 11,134,893 B2
(45) Date of Patent: Oct. 5, 2021

(54) LIMB MOVEMENT GESTURE JUDGMENT METHOD AND DEVICE

(71) Applicant: SHENZHEN UNIVERSITY, Guangdong (CN)

(72) Inventors: Kaishun Wu, Guangdong (CN); Yongpan Zou, Guangdong (CN); Jinyong Wu, Guangdong (CN); Dan Wang, Guangdong (CN); Lu Wang, Guangdong (CN)

(73) Assignee: SHENZHEN UNIVERSITY, Guangdong (CN)

( * ) Notice: Subject to any disclaimer, the term of this patent is extended or adjusted under 35 U.S.C. 154(b) by 353 days.

(21) Appl. No.: 15/757,977

(22) PCT Filed: May 16, 2017

(86) PCT No.: PCT/CN2017/084429
§ 371 (c)(1),
(2) Date: Mar. 7, 2018

(87) PCT Pub. No.: WO2018/094978
PCT Pub. Date: May 31, 2018

(65) Prior Publication Data
US 2019/0246981 A1    Aug. 15, 2019

(30) Foreign Application Priority Data

Nov. 23, 2016    (CN) .......................... 201611036676.1

(51) Int. Cl.
*A61B 5/00* (2006.01)
*A61B 5/11* (2006.01)

(52) U.S. Cl.
CPC .......... *A61B 5/6806* (2013.01); *A61B 5/0002* (2013.01); *A61B 5/1118* (2013.01);
(Continued)

(58) Field of Classification Search
CPC ............ A63B 24/0006; A63B 71/0622; A61B 5/6806; A61B 5/0002; A61B 5/1118;
(Continued)

(56) References Cited

U.S. PATENT DOCUMENTS

2011/0305369 A1*  12/2011  Bentley ................ A61B 5/1038
                                                       382/103
2013/0222565 A1   8/2013   Guerin et al.
(Continued)

FOREIGN PATENT DOCUMENTS

CN    102184549    9/2011
CN    103020598    4/2013
(Continued)

*Primary Examiner* — Malina D. Blaise
(74) *Attorney, Agent, or Firm* — JCIPRNET (57) ABSTRACT

The invention relates to a limb movement gesture judgment method, which comprises the following steps: a plurality of sensors worn on a moving wrist output induction signals generated by the sensors, and a data packet is formed and sent; the overall state of the multiple induction signals in the received data packet is compared with pre-stored movement type templates, so that the movement type of the moving wrist is determined; standard parameters of the sensor data about the movement type are obtained and separately compared with the multiple received sensor data, whether the movement gesture of the moving limb is normal or not is judged according to the degree of deviation of one or more induction signals from the corresponding standard parameters, and a corresponding prompt message is provided; wherein, the induction signals include a direction acceleration signal, a direction angle acceleration induction signal, and a pressure induction signal. The limb movement gesture judgment method and device have the following beneficial effects of being free of time and place limitations and low in cost.

10 Claims, 3 Drawing Sheets

(52) U.S. Cl.
CPC .......... *A61B 5/6802* (2013.01); *A61B 5/6824* (2013.01); *A61B 5/6825* (2013.01); *A61B 5/6828* (2013.01); *A61B 5/746* (2013.01); *A61B 2562/0219* (2013.01)

(58) Field of Classification Search
CPC ... A61B 5/6802; A61B 5/6824; A61B 5/6825; A61B 5/6828; A61B 5/746; A61B 2562/0219
See application file for complete search history.

(56) References Cited

U.S. PATENT DOCUMENTS

| | | | |
|---|---|---|---|
| 2014/0278220 A1* | 9/2014 | Yuen | A61B 5/02427 702/150 |
| 2015/0019135 A1* | 1/2015 | Kacyvenski | G09B 19/0038 702/19 |
| 2016/0232807 A1* | 8/2016 | Ghaffari | G09B 19/00 |
| 2017/0035327 A1* | 2/2017 | Yuen | A61B 5/02438 |
| 2017/0061817 A1* | 3/2017 | Mettler May | A61B 5/7455 |

FOREIGN PATENT DOCUMENTS

| | | |
|---|---|---|
| CN | 103637807 | 3/2014 |
| CN | 103713739 | 4/2014 |
| CN | 104147770 | 11/2014 |
| CN | 104461013 | 3/2015 |
| CN | 104888444 | 9/2015 |
| CN | 105043383 | 11/2015 |
| CN | 105797350 | 7/2016 |
| CN | 105833508 | 8/2016 |

* cited by examiner

LIMB MOVEMENT GESTURE JUDGMENT METHOD AND DEVICE

CROSS-REFERENCE TO RELATED APPLICATION

This application is a 371 application of an international PCT application serial no. PCT/CN2017/084429, filed on May 16, 2017, which claims priority to and the benefit of China Patent Application No. CN201611036676.1, filed on Nov. 23, 2016. The entirety of each of the abovementioned patent applications is hereby incorporated by reference herein and made a part of this specification.

BACKGROUND OF THE INVENTION

Technical Field

The invention relates to movement process recording equipment, in particular to a limb movement gesture judgment method and device.

Description of Related Art

With the constant improvement of the living standard, the health care consciousness of people is continuously enhanced, and more and more people take part in national fitness. Physical exercise based on limb movement is becoming more and more popular among people. Fitness is an extremely professional sports activity, and the fitness effect can be severely affected if limb motions are incorrect or the exercise amount is too large or too small, and even opposite effects can be caused, for example, muscle strain or joint injuries or other negative consequences can be caused. In the prior art, a method for avoiding the situation was to employ a professional fitness instructor for field guidance, however, the method has field and cost limitations and cannot meet the requirements of people for fitness anytime and anywhere. Therefore, it is necessary to provide a method which is convenient to use and can judge limb movement gestures and provide standard movement gestures anytime and anywhere.

BRIEF SUMMARY OF THE INVENTION

To overcome the defects of high cost and field limitations of the prior art, the invention provides a limb movement gesture judgment method and device which are low in cost and free of time and place limitations.

According to the technical scheme adopted by the invention: a limb movement gesture judgment method comprises the following steps:

a plurality of sensors worn on a moving limb output induction signals generated by the sensors, and then a data packet is formed and sent;

the various received sensor data are matched with movement type templates which are pre-stored locally and represent various movement types, and the movement type of the current motion is determined according to the degree of similarity;

standard parameters of the induction signals about the movement type are obtained from movement parameter modules which are stored locally and correspond to the movement type, and are separately compared with the multiple received induction signals, whether the movement gesture of the moving limb is normal or not is judged according to the degree of deviation of one or more induction signals from the corresponding standard parameters, and a corresponding prompt message is provided;

wherein, the induction signals include a direction acceleration induction signal, a direction angle acceleration induction signal and a pressure induction signal.

Furthermore, with the coordinate system of the corresponding sensor as the reference system, the induction signals include acceleration signals in the X-axis direction, the Y-axis direction and the Z-axis direction on the three-dimensional rectangular coordinates, angular acceleration signals in the X-axis direction, the Y-axis direction and the Z-axis direction, magnetic field intensity signals in the X-axis direction, the Y-axis direction and the Z-axis direction, and pressure signals output by pressure sensors worn on different positions of the moving limb; the sensors include a three-axis accelerometer, a three-axis magnetometer, a three-axis gyroscope and/or the pressure sensors.

Furthermore, a data packet is formed by the multiple generated induction signals, and each induction signal has a fixed position in the data packet.

Furthermore, when the movement type is determined, the similarities between different dimensional data readings of each sensor and the dimensional data of corresponding sensors in the multiple pre-stored movement type templates are matched separately, the similarity state of the dimensional data of each sensor in each movement type template is recorded, and the movement type represented by the movement type template with the maximum similarity is the current movement type of the limb.

Furthermore, when whether the movement gesture of the limb is normal or not is judged, induction signals obtained by the sensors set for the selected movement type are compared with corresponding standard parameter values of the induction signals in the movement parameter template corresponding to the movement type one by one, and whether the induction signals deviate from the standard parameters or not is judged; if the degree of deviation exceeds a set threshold value, it is judged that the movement gesture of the limb is abnormal, a prompt is provided, and animations or images for the standard motion are displayed.

Furthermore, each movement type template is the set of dimensional data of various sensors obtained when the limb makes the standard motion of a certain movement type, and each movement parameter template includes the standard values of dimensional data output by sensors set when the limb makes the standard motion of a certain movement type.

Furthermore, the limb movement gesture judgment method further comprises the following steps:

when the limb makes motions of a certain movement type normally, the number of the normal motions is recorded and displayed;

the number of motions of a certain movement type completed in a set time is set, and after the set number of motions of the movement type are completed, the set movement type is marked.

The invention further relates to a device for realizing the above method, and the device comprises:

a sensor unit, wherein the sensor unit is used for making a plurality of sensors worn on a moving limb output induction signals generated by the sensors, and then a data packet is formed and sent;

a movement type judgment unit, wherein the movement type judgment unit is used for matching the various received sensor data with movement type templates which are pre-stored locally and represent various movement types and judging the movement type of the current motion according to the degree of similarity;

a limb gesture judgment unit, wherein the limb gesture judgment unit is used for obtaining standard parameters of all induction signals about the movement type from movement parameter modules which are stored locally and correspond to the movement type, comparing the standard parameters with the multiple received induction signals separately, judging whether the movement gesture of the moving limb is normal or not according to the degree of deviation of one or more induction signals from the corresponding standard parameters, and providing a corresponding prompt message;

wherein, the induction signals include a direction acceleration induction signal, a direction angle acceleration induction signal and a pressure induction signal.

Furthermore, with the coordinate system of the corresponding sensor as the reference system, the induction signals include acceleration signals in the X-axis direction, the Y-axis direction and the Z-axis direction on the three-dimensional rectangular coordinates, angular acceleration signals in the X-axis direction, the Y-axis direction and the Z-axis direction, magnetic field intensity signals in the X-axis direction, the Y-axis direction and the Z-axis direction, and pressure signals output by pressure sensors worn on different positions of the moving limb; the sensors include a three-axis accelerometer, a three-axis magnetometer, a three-axis gyroscope and/or the pressure sensors.

Furthermore, the device comprises:

a recording unit, wherein the recording unit is used for recording and displaying the number of normal motions completed when the limb makes the motions of the certain movement type normally;

a setting and marking unit, wherein the setting and marking unit is used for setting the number of motions of a certain movement type completed in a set time and marking the set movement type after the set number of motions of the movement type are completed.

The limb movement gesture judgment method and device of the invention have the following beneficial effects that the sensors are arranged on a wearable device, the wearable device can be worn on the limb during limb movement, in this way, when the limb moves, the sensors output induction signals, and then a data packet is formed and sent; the multiple induction signals in the obtained data packet are compared with the stored movement type templates and the parameters in the movement parameter templates so that the movement type can be determined according to the comparison result with the movement type templates and whether the motion made by the limb is standard or not can be judged according to the comparison result with the parameters in the movement parameter templates, and accordingly, an improvement prompt or standard motion images are provided. Therefore, the limb movement gesture judgment method and device are free of time and place limitations and low in cost.

DETAILED DESCRIPTION OF THE INVENTION

A further description of the embodiment of the invention is given with the accompanying drawings as follows.

Figure 1:
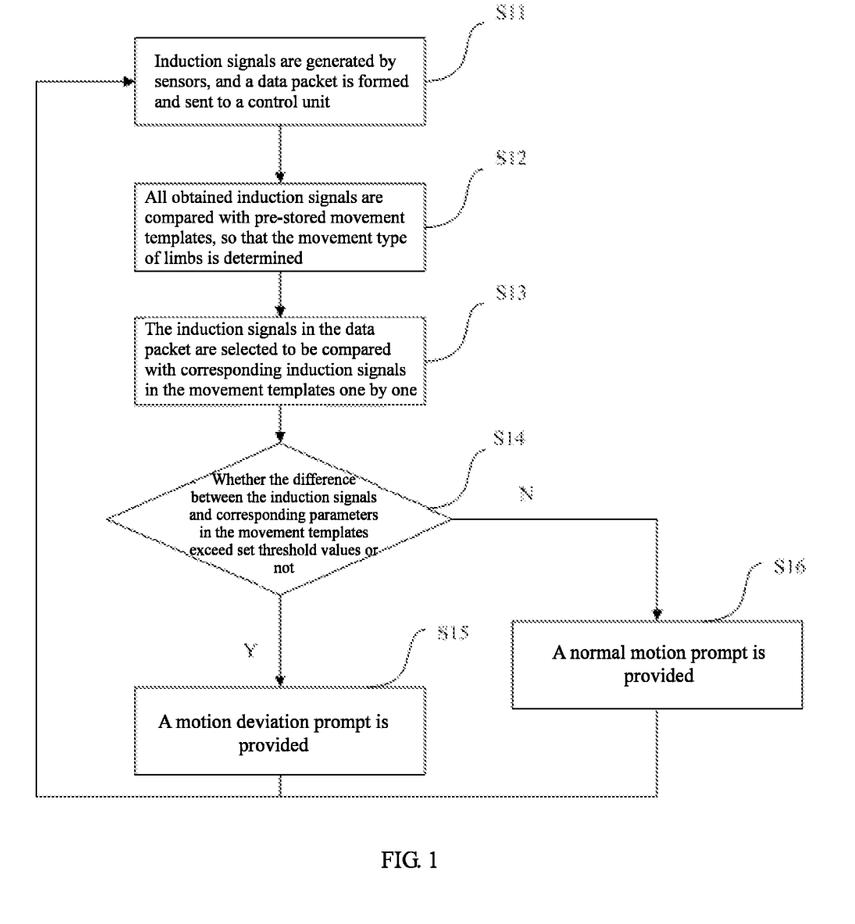
FIG. 1 is a flow diagram of the method in the embodiment of a limb movement gesture judgment method and device of the invention.

As is shown in FIG. 1, in the embodiment of a limb movement gesture judgment method and device of the invention, the limb movement gesture judgment method comprises the following steps that:

In step S11, sensors generate induction signals, and then a data packet is formed and sent to a control unit, specifically, in the step, multiple sensors worn on a moving limb output induction signals generated by the sensors, and then a data packet is formed and sent. Basically, when people do exercise, limbs definitely move; in the embodiment, the sensors are arranged on protectors or devices which can be attached to limbs during exercise, such as gloves or wrist guards or knee guards worn during exercise, different pressures or tensions can be applied to the positions where the protectors or devices attached to the limbs are located according to different movement types when the limbs move, and thus induction signals output by the sensors located at the positions can accurately show the current movement gestures of the limbs. In the embodiment, the induction signals include a direction acceleration induction signal, a direction angle acceleration induction signal, a magnetic field intensity signal and a pressure induction signal.

In the embodiment, for the several induction signals, each signal can have only one direction, however, although the movement state of the limb can be judged, only several limited motions such as pressing and arm bending can be judged. For widening the application range of the method in the embodiment to the greatest extent, the preferred option is to specify the content shown by each induction signal, namely each induction signal is divided into different components. For achieving the effect, with the coordinate system of the corresponding sensor as the reference system, the induction signals include acceleration signals in the X-axis direction, the Y-axis direction and the Z-axis direction on the three-dimensional rectangular coordinates, angular acceleration signals in the X-axis direction, the Y-axis direction and the Z-axis direction, magnetic field intensity signals in the X-axis direction, the Y-axis direction and the Z-axis direction, and pressure signals output by pressure sensors worn on different positions of the moving limb; the sensors used for obtaining the induction signals can be one or the combination of more of a three-axis accelerometer, a three-axis magnetometer, a three-axis gyroscope and pressure sensors, and the sensors can be arranged on identical or different positions. That is to say, with the coordinate system of the corresponding sensor as the reference system, each of the acceleration induction signal, the angular acceleration induction signal, the magnetic field intensity induction signal and the pressure induction signal is divided into three components along the X axis, the Y axis and the Z axis on the three-dimensional rectangular coordinates, and thus at least twelve induction signals are obtained finally, namely each induction signal is specified in three directions.

Figure 2:
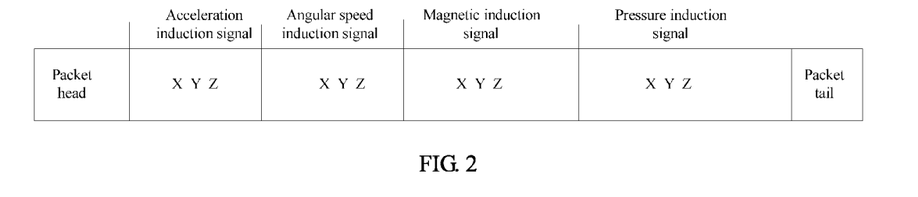
FIG. 2 is a structural diagram of a data packet of induction signals in one case in the embodiment.

In the embodiment, the induction signals are generated on the protectors or clothes worn on the limbs, due to time and use limitations, the induction signals need to be transmitted to the control unit which can process the signals, generally, the control unit is arranged on a mobile terminal, and thus the induction signals need to be transmitted to the mobile terminal from the protectors or the clothes. To transmit the signals conveniently, in the embodiment, a data packet is formed by the multiple induction signals separately output by the multiple sensors, and in the data packet, each induction signal has a fixed position. FIG. 2 shows an approximate structure of the data packet in one case of the embodiment. As is shown in FIG. 2, X, Y and Z respectively represent the three components of each induction signal on the rectangular coordinates along the X axis, the Y axis and the Z axis. FIG. 2 clearly shows that the position of each induction signal in the data packet is fixed, and the position of each component in the induction signal is also fixed. In this way, the control unit can easily find each induction signal, and all the induction signals can be processed easily.

Data or data packets can be transmitted through a wired method or a wireless method in the prior art, such as Bluetooth or WiFi.

In step S12, all the obtained induction signals are compared with pre-stored movement templates, so that the movement type of the limb is determined, specifically, in the step, when the movement type is determined, the similarities between different dimensional data readings of each sensor and the dimensional data of corresponding sensors in the multiple movement type templates are matched separately, the similarity state of the dimensional data of each sensor in each movement type template is recorded, and the movement type represented by the movement type template with the maximum similarity is the current movement type of the limb.

In the embodiment, each movement type template is the set of different dimensional data of all the sensors obtained when the limb makes the standard motion of a certain movement type, in other words, each movement type template includes all dimensional data of all the sensors, however, when the limb makes motions of the movement type, it is possible that no induction signal is output by certain sensors actually or induction signals on certain dimensions of certain sensors are not output actually, and thus the output is zero. Similarity judgment in this step actually refers to the judgment on whether the obtained induction signals are the same as data in the movement type templates or not. For example, suppose that two sensors in all are adopted for a certain movement type, the component of the sensor A in the X-axis direction is zero, and the component of the sensor B in the Y-axis direction is zero, it is judged that a received signal is similar to data in one movement type template if the component of the sensor A in the X-axis direction in the received induction signal is zero and the component of the sensor B in the Y-axis direction in the received induction signal is also zero; it is judged that the received induction signal is not similar to data in the movement type template if either the component of the sensor A in the X-axis direction or the component of the sensor B in the Y-axis direction in the received induction signal is not zero. In a case where many sensors are adopted and each sensor has many dimensionalities, judgments are made in the same way. In general, the more the similar items between received induction signals and the movement type templates are, the higher the degree of similarity is.

As the movement types basically include all common fitness motions, in the embodiment, multiple movement type templates are provided, and induction signal data in each induction signal data packet needs to be compared with the multiple movement type templates one by one so that the movement type template with the maximum similarity can be found. In the embodiment, if the matched movement type still cannot be found after all the stored movement type templates are traversed, namely a similar movement type template cannot be found, the reasons for the result are generally that the motions cannot be judged or the motions are severely distorted or the sensors have broken down, and for any reason, step S15 needs to be executed to provide a motion deviation prompt. Under this circumstance, step S13 and step S14 definitely cannot be executed.

In step S13, the induction signals in the data packet are selected to be compared with the corresponding induction signals in the movement parameter templates one by one, specifically, in the step, the standard parameter values of the induction signals in the movement parameter template corresponding to the movement type are obtained and separately compared with the multiple received induction signals, and whether the movement gesture of the moving limb is normal or not is judged according to the degree of deviation of one or more induction signals from the corresponding standard parameters; in the embodiment, each movement type corresponds to one movement parameter module, and each movement parameter module includes values of the induction signals generated by all the sensors when the limb makes the standard motion of a certain movement type; different from the movement type templates, the movement parameter module corresponding to one movement type only includes dimension signals which can be generated by the sensors in the movement process, for example, three sensors are possibly adopted in all, however, only two sensors output induction signals during movement of a certain type, only data on two dimensions from one sensor are available, in this case, the movement parameter module only includes three dimensional data parameters from one sensor and two dimensional data parameters from one sensor and does not include dimensional data from the sensor outputting no induction signal. In other words, each movement type parameter module is the set of various induction signals which can be generated during movement of the type. For example, when a professional athlete makes a certain motion, induction signals generated when the professional athlete makes the motion are recorded and gathered together in a set sequence, and then one movement type template can be obtained. All the movement type templates are obtained and stored in the control unit in advance. In the embodiment, when whether the movement gesture of the limb is normal or not is judged, the induction signals obtained at present are compared with the standard parameter values of induction signals of the same type in the matched movement type parameter template, and then whether the obtained induction signals deviate from the standard parameters or not is judged; if the degree of deviation exceeds a set threshold value, the degree of deviation is recorded, and the next induction signal is judged till all induction signals generated by the motion or all the induction signals in the sent data packet are judged. As multiple induction signals are generated by one motion, it can be identified that the limb motion or the limb gesture is abnormal when one induction signal is abnormal, or it is identified that the limb motion or the limb gesture is abnormal only when a set number of induction signals are abnormal, and the judgment standard depends on the requirements of users. In addition, threshold values used when the induction signals are judged are also preset and can be identical or different, and the threshold values can also be set as percentages of certain parameters of the induction signals.

In step S14, whether the difference values between the multiple induction signals and the corresponding parameters in the movement type templates exceed set threshold values or not is judged. If yes, step S15 is executed, and if not, step S16 is executed; in this step, the allowable number of difference values between induction signals and the corresponding parameters which exceed the set threshold values can be preset.

In step S15, a motion deviation prompt is provided, specifically, in this step, under the condition that the limb motion is regarded as abnormal, the abnormal motion prompt is provided, and animations or images for the standard motion are displayed.

In step S16, a normal motion prompt is provided, specifically, in this step, under the condition that the limb motions are regarded as normal, the motions are counted, and the abnormal motion prompt is provided. What is worth mentioning is that after step S16 or step S15 is executed, step S11 is executed again to judge the gesture of the next motion or the gesture of the next half part of the same motion.

In the embodiment, the judgment on one limb motion (or fitness motion) is achieved through the above steps, namely, each fitness motion of users can be judged, and correct motion prompts can be provided. Of course, after a set of fitness motions (or multiple repeated motions) are completed, the quality of the set of completed motions can be judged according to the judgment on each of the set of motions.

In the embodiment, the limb movement gesture judgment method can also comprise the following steps:

the number of motions of a certain movement type completed in a set time is set, after the set number of motions of the movement type are completed, the set movement type is marked, and when the limb makes motions of a certain movement type normally, the number of normal motions is recorded and displayed.

Based on the above method, the calories can be calculated, and fitness plans can be recommended so that users can use the method more conveniently.

Figure 3:
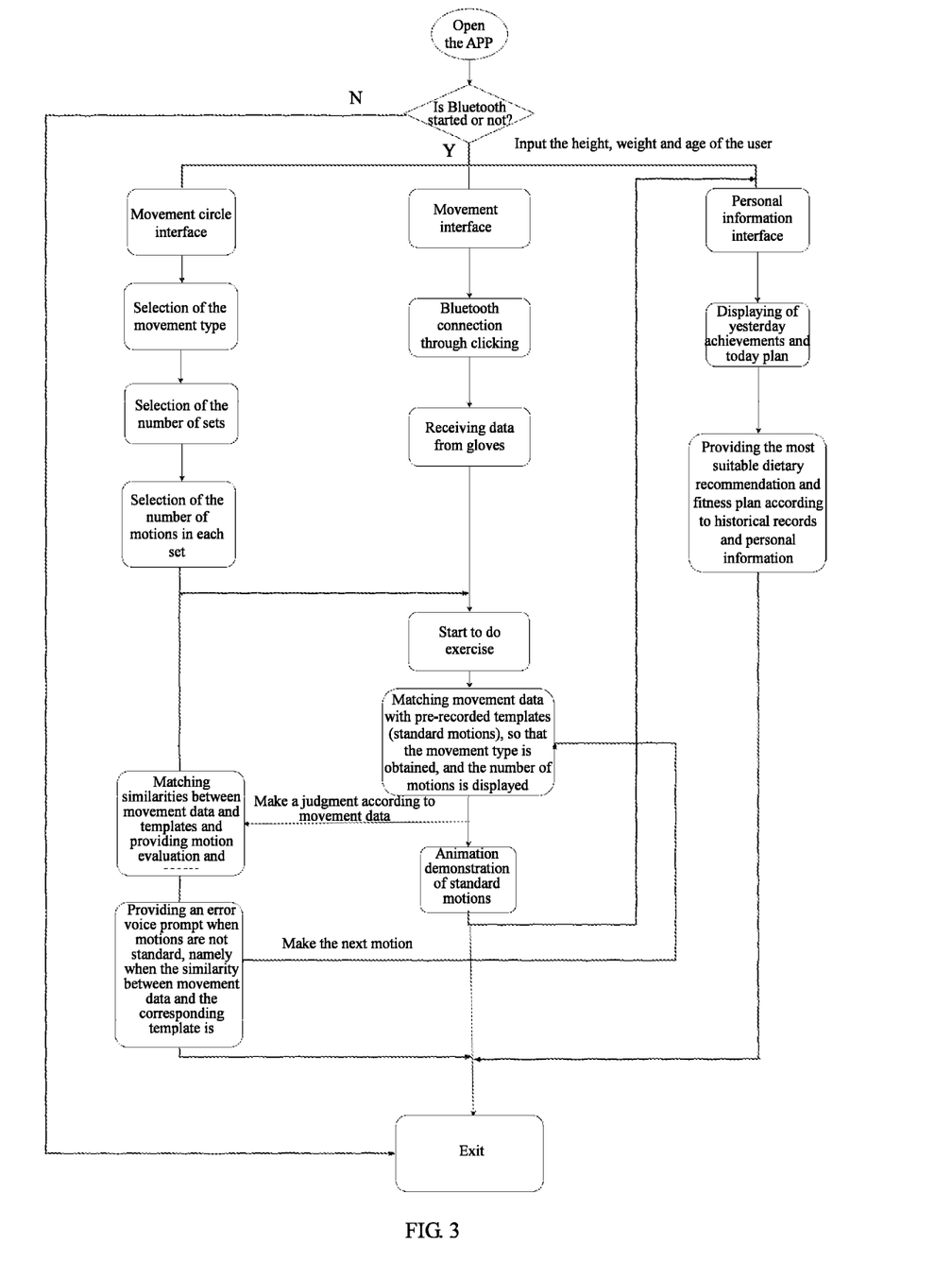
FIG. 3 is an application flow diagram of the judgment method applied to an APP in one case in the embodiment.

In the embodiment, a better approach to realize the above method is to integrate the main parts (except the sensors and the data transmission part) onto an application (APP). The APP can be applied to any mobile terminal, and thus users can verify whether their fitness motions are correct or not anytime and anywhere and fitness motions can be guided. FIG. 3 shows the operating process of an APP adopting the method in the embodiment. The process is as follows.

A user clicks a start button, and the Bluetooth of the mobile phone of the user is started after the user clicks the button; then the mobile phone starts to search for nearby Bluetooth, and the Bluetooth of the fitness gloves (each provided with at least one sensor) is selected by the user to be connected with the Bluetooth of the mobile phone; after the Bluetooth of the fitness gloves is successfully connected with the Bluetooth of the mobile phone, the mobile phone continuously receives induction signal data (namely fitness data) transmitted from the fitness gloves, the induction signals indicate the limb motions of the user during exercise, the APP continuously analyzes the fitness data of the user, and in one case, the fitness gloves send nine-axis data of an MPU and data of pressure sensors to the mobile phone (on which the APP is mounted). In the space divided by a spatial rectangular coordinate system, the nine-axis data refer to accelerations in the X-axis direction, the Y-axis direction and the Z-axis direction, angular accelerations in the X-axis direction, the Y-axis direction and the Z-axis direction and magnetic field intensities in the X-axis direction, the Y-axis direction and the Z-axis direction; data from the three pressure sensors are also transmitted, and thus data on the twelve dimensions in all are transmitted.

After the user clicks the start button, fitness motion templates, including data on twelve dimensions (regarded as data generated when limbs make standard motions) obtained when a professional does exercise, have already been stored in the program. Movement data of the user are matched with the templates continuously when the user does exercise, so that the similarities between the movement data and the templates are checked, and the movement type represented by the template having the maximum similarity with the movement data of the user is judged as the movement type of motions made by the user.

After the movement type is judged according to the movement data of the user, the movement data of the user are matched with the specific movement type repeatedly to calculate the similarity, and thus evaluation is provided to indicate whether the motions are standard or not.

The motions are scored according to the similarity between the movement data and the specific template and the motion speed, and a voice prompt is broadcast if both the motion evaluation and the motion score are low.

The user can select the corresponding type, number of sets, number of times and the like of expected fitness motions before making motions. If the user selects the options, the number of sets of motions completed by the user and the number of motions completed in each set can be displayed and broadcast.

Demonstration animations of standard motions can also be displayed, and thus references of standard motions are provided for users having no idea of standard motions.

The user can also input identity information into the APP so that the APP can provide the most scientific and suitable personal fitness plan and dietary recommendation according to the condition and historical fitness records of the user. The most scientific and suitable personal fitness plans can be provided for users according to different conditions and historical fitness records of users, and the most scientific and suitable personal dietary recommendations can also be provided for users according to different conditions and historical fitness records of users. In addition, users can also check previous fitness records.

Figure 4:
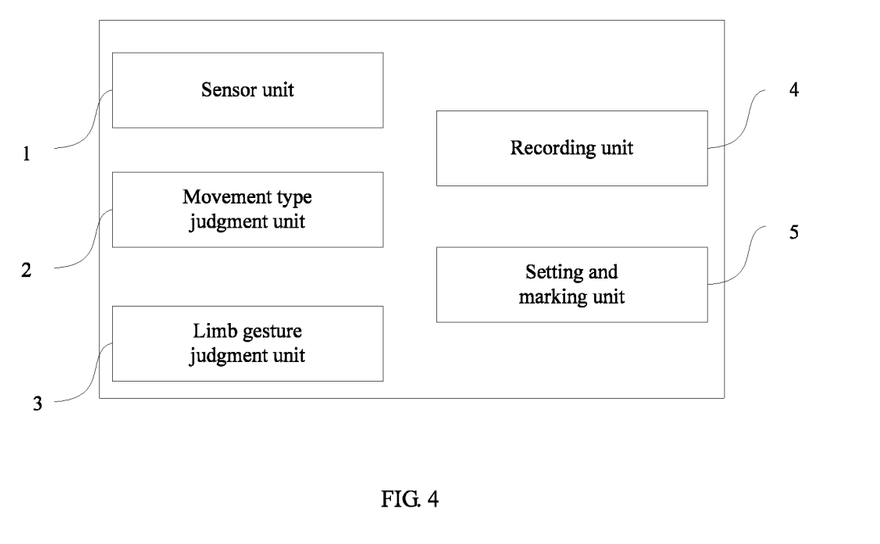
FIG. 4 is a structural diagram of the device in the embodiment.

In the embodiment, a device for realizing the above method is also disclosed, as is shown in FIG. 4, the device comprises a sensor unit 1, a movement type judgment unit 2 and a limb gesture judgment unit 3, wherein the sensor unit 1 is used for making a plurality of sensors worn on a moving limb output induction signals generated by the sensors, and then a data packet is formed and sent; the movement type judgment unit 2 is used for matching the various received sensor data with movement type templates which are pre-stored locally and represent various movement types and judging the movement type of the current motion according to the degree of similarity; the limb gesture judgment unit 3 is used for obtaining standard parameters of all induction signals about the movement type from movement parameter modules which are stored locally and correspond to the movement type, comparing the standard parameters with the multiple received induction signals separately, judging whether the movement gesture of the moving limb is normal or not according to the degree of deviation of one or more induction signals from the corresponding standard parameters, and providing a corresponding prompt message; the induction signals include a direction acceleration induction signal, a direction angle acceleration induction signal and a pressure induction signal. Furthermore, with the coordinate system of each sensor as the reference system, the induction signals include acceleration signals in the X-axis direction, the Y-axis direction and the Z-axis direction on the three-dimensional rectangular coordinates, angular acceleration signals in the X-axis direction, the Y-axis direction and the Z-axis direction, magnetic field intensity signals in the X-axis direction, the Y-axis direction and the Z-axis direction, and pressure signals output by pressure sensors worn on different positions of the moving limb; the sensors include a three-axis accelerometer, a three-axis magnetometer, a three-axis gyroscope and/or the pressure sensors.

In addition, the device further comprises a recording unit 4 and a setting and marking unit 5, wherein the recording unit 4 is used for recording and displaying the number of normal motions when the limb makes the normal motions of the certain movement type; the setting and marking unit is used for setting the number of motions of a certain movement type completed in a set time and marking the set movement type after the set number of motions of the movement type are completed.

The above embodiment only shows several execution modes of the invention and is specifically described in detail, however, the scope of the invention patent is not limited to the above embodiment. What needs to be pointed out is that for those ordinarily skilled in the field, various transformations and improvements can be made without deviating from the concept of the invention, and all the transformations and improvements are within the protection scope of the invention. Therefore, the protection scope of the patent is subject to the claims attached to the description.

What is claimed is:

1. A limb movement gesture judgment method, comprising the following steps:
    generating and outputting induction signals by a plurality of sensors configured to be worn on a moving limb, wherein the induction signals include a direction acceleration induction signal, a direction angle acceleration induction signal and a pressure induction signal;
    forming and sending a data packet by the sensors;
    receiving and matching the induction signals from the data packet, by a processor, with a plurality of movement type templates which are pre-stored locally and represent various movement types;
    determining, by the processor, a movement type of a current motion represented by a selected movement type template which is one of the plurality of the movement type templates and with a maximum similarity with the current motion according to a degree of similarity;
    obtaining, by the processor, corresponding standard parameters of the induction signals about the movement type from a movement parameter template which are stored locally and correspond to the movement type;
    comparing, by the processor, the corresponding standard parameters with the induction signals;
    judging, by the processor, whether a movement gesture of the moving limb is within a set threshold value according to a degree of deviation of one or more of the induction signals from the corresponding standard parameters; and
    providing, in a display, a corresponding prompt message of the moving limb when the degree of deviation exceeds the set threshold value, the corresponding prompt message is provided indicating that the movement gesture of the moving limb is regarded as abnormal, and animations or images for a standard motion of the moving limb are displayed.

2. The limb movement gesture judgment method according to claim 1, wherein with a coordinate system of a corresponding sensor as a reference system, the induction signals include acceleration signals in an X-axis direction, a Y-axis direction and a Z-axis direction on three-dimensional rectangular coordinates, angular acceleration signals in the X-axis direction, the Y-axis direction and the Z-axis direction, magnetic field intensity signals in the X-axis direction, the Y-axis direction and the Z-axis direction, and the pressure induction signals output by pressure sensors worn on different positions of the moving limb; the sensors include a three-axis accelerometer, a three-axis magnetometer, a three-axis gyroscope and/or the pressure sensors.

3. The limb movement gesture judgment method according to claim 2, wherein the data packet is formed by the induction signals, and each induction signal has a fixed position in the data packet.

4. The limb movement gesture judgment method according to claim 3, wherein in determining the movement type of the current motion, the similarities between different dimensional data readings of each of the sensors and the dimensional data of the corresponding sensors in the plurality of movement type templates are matched separately, a similarity state of dimensional data of each sensor in each of the plurality of movement type templates is recorded, and the movement type represented by the selected movement type template with the maximum similarity is a current movement type of the limb.

5. The limb movement gesture judgment method according to claim 4, wherein before judging whether the movement gesture of the limb is within the set threshold value, the induction signals obtained by the sensors set for the selected movement type are compared with the corresponding standard parameters of the induction signals in the movement parameter template corresponding to the movement type one by one, and whether the induction signals deviate from the corresponding standard parameters or not is judged; if the degree of deviation exceeds the set threshold value, the corresponding prompt message is provided, and animations or images for the standard motion are displayed.

6. The limb movement gesture judgment method according to claim 5, wherein each of the plurality of movement type templates is the set of dimensional data of various sensors obtained when the limb makes the standard motion of a certain movement type, and the movement parameter template includes the standard values of dimensional data output by sensors set when the limb makes the standard motion of a certain movement type.

7. The limb movement gesture judgment method according to claim 6, wherein further comprising the following steps:
    recoding and displaying a number of the motions, by the processor, when the limb makes motions of the certain movement type within the set threshold value;
    setting a number of motions, by the processor, of the certain movement type completed in a set time; and
    marking the set movement type, by the processor, after the set number of motions of the certain movement type are completed.

8. A device for realizing the limb movement gesture judgment method of claim 1, wherein the processor is configured to:
    make the plurality of sensors worn on the moving limb output induction signals generated by the plurality of sensors, and then the data packet is formed and sent by the plurality of sensors, wherein the induction signals include the direction acceleration induction signal, the direction angle acceleration induction signal and the pressure induction signal;

receive and match the induction signals from the data packet with the plurality of movement type templates which are pre-stored locally and represent various movement types;

determine the movement type of the current motion represented by the selected movement type template which is one of the plurality of the movement type templates and with the maximum similarity with the current motion according to the degree of similarity; and obtain the corresponding standard parameters of all the induction signals about the movement type from movement parameter templates which are stored locally and correspond to the movement type, compare the corresponding standard parameters with the induction signals separately, judge whether the movement gesture of the moving limb is within the set threshold value according to the degree of deviation of one or more of the induction signals from the corresponding standard parameters, and provide the corresponding prompt message in the display.

9. The device according to claim 8, wherein with the coordinate system of the corresponding sensor as the reference system, the induction signals include acceleration signals in the X-axis direction, the Y-axis direction and the Z-axis direction on the three-dimensional rectangular coordinates, angular acceleration signals in the X-axis direction, the Y-axis direction and the Z-axis direction, magnetic field intensity signals in the X-axis direction, the Y-axis direction and the Z-axis direction, and the pressure signals output by pressure sensors worn on different positions of the moving limb; the sensors include the three-axis accelerometer, the three-axis magnetometer, the three-axis gyroscope and/or the pressure sensors.

10. The device according to claim 9, the processor is being further configured to:

record and display number of the motions completed when the limb makes the motions of a certain movement type within the set threshold value; and set the number of motions of the certain movement type completed in a set time and mark the set movement type after the set number of motions of the certain movement type are completed.

* * * * *